United States Patent [19]

Wall

[11] Patent Number: 4,868,285
[45] Date of Patent: Sep. 19, 1989

[54] ANTIBIOTIC PRODUCTION

[75] Inventor: Wilfred F. Wall, Loudwater, England

[73] Assignee: Glaxo Group Limited, London, England, United Kingdom

[21] Appl. No.: 3,948

[22] Filed: Jan. 16, 1987

[30] Foreign Application Priority Data

Jan. 16, 1986 [GB] United Kingdom ................ 8600952

[51] Int. Cl.$^4$ .......................... C07K 7/50; C07K 1/14; C07K 9/00; A61K 35/74
[52] U.S. Cl. .................................. 530/317; 530/322; 530/344; 424/123; 424/124; 435/71
[58] Field of Search ...................... 530/317, 322, 344; 424/118, 123, 124; 435/71

[56] References Cited

U.S. PATENT DOCUMENTS 3,067,099 12/1962 McCormick et al. .............. 424/124

OTHER PUBLICATIONS

Yang et al., Chem. Abstr. vol. 103, No. 129068c, (1985).
Sitrim et al., Chem. Abstr. vol. 102, No. 165245w, (1985).
Zhou et al., Chem. Abstr., vol. 106, No. 23154z, (1987).

Primary Examiner—Delbert K. Phillips
Assistant Examiner—Christina Chan
Attorney, Agent, or Firm—Bacon & Thomas

[57] ABSTRACT

Imidazole/vancomycin complexes are prepared by containing an imidazole, preferably imidazole or N-methylimidazole, with a member of the vancomycin family, preferably Vancomycin itself.

The complexes are useful in the purification of vancomycin.

14 Claims, No Drawings

ANTIBIOTIC PRODUCTION

This invention relates to improvements in the production of vancomycin antibiotics.

The vancomycins are a family of closely related glycopeptides [Barna and Williams Ann. Rev. Microbiol, 38, 339 (1984)]. They are inhibitors of bacterial cell wall synthesis and are particularly useful in combating bacterial infections caused by Gram positive organisms, especially Gram positive cocci. The most important member of the vancomycin family commercially is Vancomycin itself, which is a complex of several glycopeptides that is produced by fermentation of *Nocardia orientalis* (formerly known as *Streptomyces orientalis*).

In general, the vancomycins are amphoteric and form salts, for example acid addition salts such as hydrochlorides. As used herein, the term "vancomycin" refers to all glycopeptide antibiotics that belong to the vancomycin family; the term "Vancomycin" is used to denote the antibiotic obtained from *Nocardia orientalis* and which lends its name to the group as a whole (see Barna and Williams, loc cit). Both "vancomycin" and "Vancomycin" are to be understood to additionally include the salts of the compounds concerned.

In general, the vancomycins are derived by fermentation of producing microorganisms, and extensive purification of fermentation broths is thus required to obtain the antibiotics in forms suitable for pharmaceutical use. Existing commercial purification processes are multistage operations that have associated with them a significant amount of product loss at each stage, and are expensive to employ. There is thus a need for more efficient and more convenient methods for obtaining vancomycins from fermentation broths.

The present invention is based on our discovery that when a vancomycin is contacted in solution with an imidazole compound the two will form a complex, which then precipitates from the solution and can be easily recovered in excellent yields. In this way the vancomycin can be easily separated from other impurities present in the solution. The process may be applied to vancomycin compounds present in whole or partially purified fermentation broths and thus offers a convenient method for use in the purification of the antibiotics.

Thus, in one aspect of the invention we provide a method for separating a vancomycin from a solution thereof containing impurities, which comprises the steps of contacting said solution with an imidazole and recovering the vancomycin imidazole precipitate thus produced.

Imidazole/vancomycin complexes are novel and constitute a further aspect of the invention.

In general the precipitation is preferably carried out at a pH in the range 3 to 8, for example 4 to 6, advantageously about pH 5. The imidazoles which may be employed in the process of the invention include imidazole and substituted derivatives thereof such as N-alkylimidazoles, preferably N-($C_{1-4}$)alkylimidazoles e.g. N-methylimidazole. Such imidazoles are, in general water soluble. Imidazole is particularly preferred.

The imidazole may be either a liquid or a solid, and both forms may be used in the process of the invention. Where the imidazole is a solid, however, it is preferable to dissolve it in a suitable solvent e.g. water, prior to use. The imidazoles are relatively basic and in aqueous solutions at acid pH they will be in the protonated, i.e. salt form. The weight of the imidazole which is added to the vancomycin containing solution is not crucial but will be at least equal to the weight of vancomycin present in the solution, and, for example, will generally be two times up to ten times e.g. two times to six times, by weight of the vancomycin compound. The concentration of the vancomycin in the starting solution may be estimated by standard assay techniques, e.g. by high performance liquid chromatography (hplc).

The vancomycin containing solution will preferably be an aqueous solution of the antibiotic, but may also be a solution of the antibiotic in an organic solvent, for example a solvent such as dimethylsulphoxide.

The precipitate produced according to the invention may be recovered using conventional methods e.g. by filtration or by centrifugation. If desired, the precipitate may be washed with one or more solvents.

The desired vancomycin may be recovered free of the imidazole by, for example, redissolving the precipitate obtained according to the invention in a suitable solvent e.g. water which has been acidified with an acid such as hydrochloric acid, and reprecipitating the antibiotic using for example a non-solvent for the vancomycin e.g. an alcohol such as ethanol. The precipitated vancomycin may then be harvested e.g. by filtration. The vancomycin may be recovered in the base form or, if acid is present during precipitation, in the form of an acid addition salt, e.g. the hydrochloride.

The process according to the invention may be employed at any stage in the production of the vancomycin, for example with a whole fermentation broth or a whole broth which has been previously purified e.g. by filtration, extraction, precipitation and/or chromatography. Whole fermentation broth containing the vancomycin used as starting material may be obtained by fermentation of known producing microorganisms under conditions well-known to the art. Thus, for example, Vancomycin-containing whole broth may be obtained by fermentation of a producing strain of Nocardia orientalis e.g. *Nocardia orientalis* NRRL 2452 using the methods described in U.S. Pat. No. 3067099. Fermentation broths containing other vancomycin antibiotics may be obtained from appropriate known producing organisms by similar methods.

It will be appreciated that the purity of the vancomycin/imidazole precipitate produced according to the invention and the vancomycin obtained therefrom will depend to a large extent on the nature of the starting material used. Thus, where a previously unpurified preparation (e.g. whole fermentation broth) is used in the method of the invention the resulting precipitate will still contain impurities not required in the final product. These may be removed, either by redissolving, filtering if necessary and repeating the precipitation with the same or a different imidazole or by subjecting the precipitate to other techniques, e.g. chromatography such as adsorption chromatography and/or ion exchange chromatography. In general, however, where a partially purified vancomycin is used as a starting material in the process of the invention, the resulting precipitate can be used directly to yield the desired vancomycin in acceptable purity.

We have found the process according to the invention to be especially suitable for use with Vancomycin.

Thus, in a preferred aspect of the invention we provide a process for separating Vancomycin from an aqueous solution thereof in admixture with impurities, which comprises the steps of contacting said aqueous solution with an imidazole and recovering the Vancomycin containing precipitate thus produced.

The imidazole may be for example N-methylimidazole or, preferably, imidazole. The Vancomycin-containing solution is desirably an aqueous solution of the antibiotic.

We have used the method according to the invention to develop a process suitable for the purification of Vancomycin present in the fermentation broth obtained from strains of *Nocardia orientalis* producing Vancomycin. The new process involves an initial partial purification of the fermented antibiotic by filtration and adsorption chromatography, the purification then being completed by reaction with an imidazole. The process is simple to operate and provides Vancomycin in good yields substantially free of impurities.

Thus, in another aspect of the invention we provide a process for the preparation of Vancomycin which comprises the steps of (1) filtering a fermentation broth obtained from a strain of *Nocardia orientalis* producing Vancomycin and collecting the filtrate, (2) contacting the filtrate with a non-functional or intermediate polarity synthetic polymeric resin to adsorb the Vancomycin, (3) eluting the Vancomycin from the resin, (4) contacting the Vancomycin eluted with an imidazole and recovering the precipitated Vancomycin thus produced and (5) recovering the Vancomycin from the precipitate.

The starting fermentation broth may be obtained by cultivation of a strain of *Nocardia orientalis* producing Vancomycin such as *Nocardia orientalis* NRRL 2452. The broth is harvested and may then be filtered, e.g. using a diatomacous filter aid such as Dicalite and at an alkaline pH of from, for example, pH 7.2 to 9.0 to remove solid impurities and mycelia. The pH of the filtrate may then be adjusted to around pH 7.0, the filtrate is then applied to a non-functional or intermediate polarity synthetic polymeric resin and the Vancomycin adsorbed thereon. The adsorbent may be an acrylic ester resin e.g. Amberlite XAD-7 or more preferably a styrene divinylbenzene resin, for example, a Kastel S112 resin. The Vancomycin is eluted from the resin with a suitable solvent, for example an aqueous alcohol containing an acid, e.g. aqueous methanol or propanol containing hydrochloric acid. In some cases, the resin treatment may be in two stages, if desired, using different resins. If desired, the resulting Vancomycin rich eluate may be concentrated e.g. by evaporation of the solvent under reduced pressure. The Vancomycin may, if desired, be precipitated at this stage, e.g. by addition of acidic acetonitrile. In general, however, it is more convenient to use the eluate directly in the following precipitation step.

The Vancomycin is next contacted, with an imidazole compound, preferably in solution in a suitable solvent such as water. A Vancomycin/imidazole complex precipitates and may be then harvested e.g. by filtration. Excess of the imidazole present with the complex may be removed by washing with one or more solvents such as a ketone e.g. acetone.

N-methylimidazole or, preferably, imidazole are particularly suitable for use in this part of the process, since, on contact with Vancomycin, crystals containing Vancomycin and the imidazole are readily produced. These may be easily harvested, and substantially pure Vancomycin may be recovered from them. Crystals comprising Vancomycin and imidazole or N-methylimidazole in a 1:1 molar ratio are a particularly useful aspect of the invention.

The Vancomycin may be recovered from the harvested precipitate by redissolving the latter in a suitable solvent e.g. water containing an acid, such as hydrochloric acid for example at about pH 2. The Vancomycin (as a salt e.g. the hydrochloride) may then be precipitated by addition of a suitable non-solvent for vancomycin compound such as an alcohol e.g. ethanol, and harvested by, for example, filtration. If desired the Vancomycin may then be further washed with, for example, diethyl ether to yield highly pure Vancomycin in salt form.

The invention is further illustrated by the following non-limiting examples. Examples 1 and 2 illustrate processes based on an imidazole contact step which have been designed to purify Vancomycin in crystalline form from fermentation broths. Examples 3 and 4 illustrate the operation of the process according to the invention with a Vancomycin starting material which has been previously purified.

In the following examples Vancomycin was assayed by hplc using a Spherisorb C6 ($5\mu$) column 15 cm$\times$0.46cm id., 12.57 column capacity factor, operating at 4000 p.s.i and at a flow rate of 3ml/min. The mobile phase was acetonitrile:ammonium dihydrogen orthophosphate solution ($NH_4H_2PO_4$, 0.01M containing sodium lauryl sulphate 2.88 g/L) 35:65 brought to pH 3 with phosphoric acid. Detection was at 220nm and the standard was Vancocin (Eli Lilly) which is Vancomycin hydrochloride containing not less than 900 $\mu$g Vancomycin per mg. (H. E. Simmons Federal Register 36(20) p 1408–1409 part 148 S 1971). "Vancocin" contains traces of other materials which are separated from the main Vancomycin peak on hplc. The main peak was taken to be due to 1000 $\mu$g/mg Vancomycin hydrochloride without further correction.

EXAMPLE 1

Harvest broth [obtained by fermentation of a Vancomycin producing strain of *Nocardia orientalis* (see e.g. U.S. Pat. No. 3067099), 43L] was adjusted from natural pH 7.5 to pH 9.0 with 40% sodium hydroxide solution and filtered using Dicalite 478 (2% v/v) filter aid and Rettenmaier cellulose bed (66 cm in diameter$\times$1.25 cm). The waste debris was resuspended in water and filtered through the same be to give a total filtrate and wash (47L); this was adjusted to pH 7.2 with hydrochloric acid.

A portion of the bulked filtration wash (45.25L) was poured onto a column (4L, approx 7.5 cm diameter x 86 cm) of Kastel S112 resin running at 8L/h. The column was washed with water (8L) and aqueous methanol (20%, 8L) and eluted with methanol/water/N hydrochloric acid (5:4:1) in 2L fractions. Fractions 2 and 3 contained most of the antibiotic (4L, Vancomycin assay 10.25 g/L) and this was stored at pH 6 (adjusted with sodium hydroxide) for 10 days during which time a crude dark brown sludge precipitated (8.67 g, Vancomycin assay 0.53 g/g).

The clear yellow supernatant liquor was adjusted to pH 5 (hydrochloric acid) and the methanol distilled under reduced pressure to give a concentrate (2.3L, Vancomycin assay 13.33 g/L). This solution (2.1L) was adjusted to pH 7.2 (sodium hydroxide) and run onto a column (4.5 cm diameter$\times$100 cm) of Amberlite XAD7 resin running at 1.5L/h. The column was washed with water (3L) and eluted with water/propan-1-ol/N hydrochloric acid (7:2:1); the Vancomycin was collected in a single fraction (1.75L) after rejecting the first eluate (2L). The antibiotic rich eluate was adjusted to pH 5 with sodium hydroxide, distilled under reduced pressure to remove the propanol and made up to 1500ml (Vancomycin assay 17.1 g/L).

A sample of concentrated eluate (900 ml) was adjusted to pH 2.5 with hydrochloric acid (6N) and poured into acetonitrile (8.1L) with stirring. After standing for 18 h at 18° C. the product was harvested by filtration, washed with acetonitrile and diethyl ether and air dried to give Vancomycin hydrochloride (Vancomycin assay 0.875 g/g).

The crude Vancomycin hydrochloride (5.0 g) was dissolved in water (50 ml) and stirred during the addition of imidazole (10 g) in water (50 ml). An initial precipitate formed which dissolved rapidly as a second white precipitate deposited; this was harvested by filtration and air-dried to give approximately 6 g of white crystals (hplc assay: imidazole 10 mol: Vancomycin 1 mol). The crystals were washed with acetone (4x25 ml) and diethyl ether (25 ml) and dried in vacuo to give white crystals (4.5 g, imidazole 1 mol: Vancomycin 1 mol. Vancomycin assay 0.96 g/g).

The Vancomycin/imidazole crystals (0.5 g) were dissolved in water (2.5 ml) by the addition of hydochloric acid (6N) to pH 2.0 and the solution added to ethyl alcohol (25 ml). After 2 h at 0° C. the precipitate was harvested by filtration, washed with diethyl ether (5 ml) and dried in vacuo to give Vancomycin hydrochloride (0.44 g, Vancomycin assay 1.04 g/g).

EXAMPLE 2

Harvest broth as described in Example 1, (3.0L) was adjusted from pH 7.4 to pH 9.0 with sodium hydroxide (6N) and filtered on a bed of Dicalite 12.5×1.25 cm and the bed washed with water. The filtrate was adjusted to pH 7.2 with hydrochloric acid (6N).

A column of resin S112 (Kastel, 100 ml, 20 mm internal diameter) was prepared by washing with methanolic alkali and acid and washing to neutrality with water. A portion of the filtered broth was run onto the column at 200 ml/h followed by water (175 ml) and the Vancomycin eluted with methanol/water/N hydrochloric acid (5,4,1). The main activity was collected in a band (100 ml, 9.165 mg/ml Vancomycin).

The bulked active fraction (96 ml) was adjusted to pH5 with sodium hydroxide (6N) and distilled under reduced pressure to remove the methanol. The aqueous residue was readjusted to 50 ml with water (Vancomycin assay 16.9 mg/ml).

A solution of imidazole in water (5 g in 5 ml water) was added to the concentrate (48 ml), the solution seeded with authentic crystals and stirred at 2° to 4° C. The crystals were harvested after 18 h by filtration, washed with a little water containing 5% imidazole and air-dried. The crystals were washed with acetone (4×5 ml) and the white residue air-dried to give a Vancomycin:imidazole complex (approx. 1:1 by hplc, 641.2 mg Vancomycin).

Treatment of the Vancomycin/imidazole crystals to remove imidazole as described in Example 1 yields Vancomycin Hydrochloride.

EXAMPLE 3

Vancomycin hydrochloride ('Vancocin' Eli Lilly, 100 mg) was dissolved in water (1 ml) and a solution of imidazole (200 mg) in water (1 ml) added. The immediate heavy white precipitate dissolved on shaking and the clear solution gradually deposited white crystals of a Vancomycin imidazole complex. After 15 min at ambient temperature the crystals were harvested by centrifugation washed with a little aqueous imidazole solution (0.5 ml, 10%), centrifuged, decanted then dried in vacuo to yield while crystals (145 mg). Vancomycin assay approx 70%, hplc assay imidazole 10 mol: Vancomycin 1 mol.

EXAMPLE 4

Vancomycin hydrochloride ('Vancocin' Eli Lilly, 100 mg) was dissolved in water (1 ml) and N-methylimidazole (0.2 ml; 326 mg) in water (1 ml) added. The initial precipitate dissolved and a white crystalline precipitate deposited. After 30 min at ambient temperature the product was harvested by centrifugation, washed with a little N-methylimidazole solution, centrifuged, decanted and dried in vacuo to give white crystals (101 mg). Vancomycin assay approx 65%. hplc assay N-methylimidazole: Vancomycin approx 10:1.

I claim:

1. A method for separating a vancomycin from a solution thereof containing impurities, which comprises the steps of contacting said solution with imidazole or an N-($C_{1-4}$)alkylimidazole and recovering the precipitate thus produced.

2. A method as claimed in claim 1 wherein vancomycin is dissolved in an aqueous medium.

3. A method as claimed in claim 2 wherein the aqueous medium is water.

4. A method as claimed in claim 1 wherein the vancomycin solution has a pH in the range 3 to 8.

5. A method as claimed in claim 4 wherein the vancomycin solution has a pH in the range 4 to 6.

6. A method as claimed in claim 5 wherein the vancomycin solution has a pH of about 5.

7. A method as claimed in claim 1 wherein the vancomycin is Vancomycin.

8. A method as claimed in claim 1 wherein after the recovery of the precipitate the vancomycin is separated therefrom by dissolving in water which has been acidified and precipitating the vancomycin by addition of a non-solvent therefor.

9. A method as claimed in claim 8 wherein the water has been acidified by the addition of hydrochloric acid.

10. A method as claimed in claim 1 wherein the solution is contacted with imidazole or N-methyl-imidazole.

11. A process for the preparation of Vancomycin which comprises the steps of:
(1) filtering a fermentation broth obtained from a Vancomycin producing strain of *Nocardia orientalis* and collecting the filtrate;
(2) contacting the filtrate with a non-functional or intermediate polarity synthetic polymeric resin to adsorb the Vancomycin;
(3) eluting the Vancomycin from the resin;
(4) contacting the eluted Vancomycin with imidazole and or an N-($C_{1-4}$)alkylimidazole recovering the precipitated complex thus produced;
(5) recovering the Vancomycin from the precipitated complex.

12. A process as claimed in claim 11 wherein the synthetic polymeric resin is an acrylic ester resin or a styrene divinylbenzene resin.

13. A process as claimed in claim 11 wherein the eluant of stage (3) is an aqueous alcohol containing an acid.

14. A process as claimed in claim 11 wherein the eluted vancomycin of stage (3) is contacted with imidazole of N-methylimidazole.

* * * * *